US008623826B2

(12) United States Patent
Trento et al.

(10) Patent No.: US 8,623,826 B2
(45) Date of Patent: Jan. 7, 2014

(54) COMPOSITIONS AND METHODS FOR TREATING CENTRALLY MEDIATED NAUSEA AND VOMITING

(75) Inventors: Fabio Trento, Como (IT); Sergio Cantoreggi, Cagiallo (CH); Giorgia Rossi, Como (IT); Roberta Cannella, Varese (IT); Daniele Bonadeo, Varese (IT)

(73) Assignee: Helsinn Healthcare S.A., Lugano/Pazallo (CH)

( * ) Notice: Subject to any disclaimer, the term of this patent is extended or adjusted under 35 U.S.C. 154(b) by 0 days.

(21) Appl. No.: 13/077,462

(22) Filed: Mar. 31, 2011

(65) Prior Publication Data
US 2012/0064153 A1 Mar. 15, 2012

Related U.S. Application Data

(63) Continuation of application No. PCT/US2010/057192, filed on Nov. 19, 2010.

(60) Provisional application No. 61/382,709, filed on Sep. 14, 2010, provisional application No. 61/262,470, filed on Nov. 18, 2009.

(51) Int. Cl.
| | |
|---|---|
| A61K 31/573 | (2006.01) |
| A61K 31/4178 | (2006.01) |
| A61P 1/08 | (2006.01) |
| A61K 9/00 | (2006.01) |
| A61K 9/20 | (2006.01) |
| A61K 9/48 | (2006.01) |
| A61K 31/496 | (2006.01) |
| A61K 31/473 | (2006.01) |

(52) U.S. Cl.
USPC .......... 514/17.7; 514/183; 514/185; 514/187; 514/188; 514/872

(58) Field of Classification Search
USPC ...................................................... 514/218
See application file for complete search history.

(56) References Cited

U.S. PATENT DOCUMENTS

| 5,202,333 | A | 4/1993 | Berger et al. |
| 5,510,486 | A | 4/1996 | Robinson, III et al. |
| 6,297,375 | B1 | 10/2001 | Bös et al. |
| 6,593,472 | B2 | 7/2003 | Hoffmann et al. |
| 6,719,996 | B2 | 4/2004 | Kuentz et al. |

FOREIGN PATENT DOCUMENTS

| WO | WO 2004/045615 A1 | 6/2004 |
| WO | WO 2004/067005 A1 | 8/2004 |
| WO | WO 2004/073714 A1 | 9/2004 |
| WO | WO 2008/049552 A1 | 5/2008 |

OTHER PUBLICATIONS

Mar. 27, 2003, Approved FDA Prescribing Information for Emend.
Ruhlmann, Christina et al., "Casopitant: a novel NK1-receptor antagonist in the prevention of chemotherapy-induced nausea and vomiting," Therapeutics and Clinical Risk Management, 2009:5 pp. 375-384.
Pellegatti, Mario et al., "Disposition and Metabolism of Radiolabeled Casopitant in Humans," Drug Metabolism and Disposition, vol. 37, No. 8, 2009, pp. 1635-1645.
Huang, Shih-Chung et al., "Neurokinin-1 receptor antagonists: a comprehensive patent survey," Expert Opin. Ther. Patents (2010) 20(8), pp. 1019-1045.
Reddy, G. Kesava et al., "Novel Neurokinin-1 Antagonists as Antiemetics for the Treatment of Chemotherapy-Induced Emesis," Supportive Cancer Therapy, Apr. 1, 2006, LNKD-PUBMED: 18632487, vol. 3, No. 3, pp. 140-142, XP002626039, ISSN: 1543-2912.
De Wit, R., "Current position of 5HT3 antagonists and the additional value of NK1 antagonists; a new class of antiemetics," British Journal of Cancer, Jun. 16, 2003, LNKD-PUBMED: 12799621, vol. 88, No. 12, pp. 1823-1827, XP002626041, ISSN: 0007-0920.
Diemunsch, P. et al., "Neurokinin-1 receptor antagonists in the prevention of postoperative nausea and vomiting," British Journal of Anaesthesia, Jul. 2009, LNKD-PUBMED: 19454547, vol. 103, No. 1, 7-13, XP002626040, ISSN: 1471-6771.
Diemunsch, Pierre et al., "Potential of Substance P Antagonists as Antiemetics," Jan. 1, 2003, Antiemetic Therapy, Basel [U.A.]: Karger, CH, pp. 78-97, XP008133831, ISBN: 978-3-8055-7547-8.
Grunberg, Steven M., et al., "Effectiveness of a single-day three-drug regimen of dexamethasone, palonosetron, and aprepitant for the prevention of acute and delayed nausea and vomiting caused by moderately emetogenic chemotherapy," Support Care Cancer: Official Journal of the Multinational Association of Supportive Care in Cancer, May 2009 LNKD-PUBMED: 19037667, vol. 17, No. 5, pp. 589-594, XP002626042, ISSN: 1433-7339.
Stathis, Marigo et al., "Inhibition of substance P-mediated responses in NG108-15 cells by netupitant and palonosetron exhibit synergistic effects," European Journal of Pharmacology 689 (2012) pp. 25-30.
Press Release, GSK provides update on regulatory filings for Zunrisa/Rezonic; Issued: Monday Sep. 28, 2009, London UK.
Warr et al., Efficacy and tolerability of aprepitant for the prevention of chemotherapy-induced nausea and vomiting in patients with breast cancer after moderately emetogenic chemotherapy. (2005) J. Clin. Oncol. 23(12):2822-2830.
Herrington et al., Randomized, placebo-controlled, pilot study evaluating aprepitant single dose plus palonosetron and dexamethasone for the prevention of acute and delayed chemotherapy-induced nausea and vomiting. (2008) Cancer 112(9):2080-2087.
Yeo et al., A randomized study of aprepitant, ondansetron and dexamethasone for chemotherapy-induced nausea and vomiting in Chinese breast cancer patients receiving moderately emetogenic chemotherapy. (2009) Breast Cancer Res. Treat. 113:529-535.
Longo et al., Palonosetron plus 3-day aprepitant and dexamethasone to prevent nausea and vomiting in patients receiving highly emetogenic chemotherapy. (2011) Support Care Cancer 19:1159-1164.
Press Release, NK1 receptor antagonist by Roche; Issued: Thursday, Feb. 23, 2006, http://leaddiscovery.blogspot.com/2006/02/nk1-receptor-antagonist-by-roche.html (leaddiscovery.co.uk).

*Primary Examiner* — Walter Webb
(74) *Attorney, Agent, or Firm* — Clark G. Sullivan; Heather M. Ettinger; Troutman Sanders LLP

(57) ABSTRACT

Provided are methods for treating nausea and vomiting in patients undergoing chemotherapy, radiotherapy, or surgery, comprising the co-administration of netupitant, palonosetron and dexamethasone.

25 Claims, 5 Drawing Sheets

COMPOSITIONS AND METHODS FOR TREATING CENTRALLY MEDIATED NAUSEA AND VOMITING

CROSS-REFERENCE TO RELATED APPLICATIONS

This application is a continuation of International Patent Application No. PCT/IB10/03106, filed Nov. 18, 2010; which claims priority to U.S. Provisional Application No. 61/262,470, filed Nov. 18, 2009; and U.S. Provisional Application No. 61/382,709, filed Sep. 14, 2010. Application Nos. 61/262,470 and 61/382,709 and PCT Application No. PCT/IB10/03106 are hereby incorporated herein by reference in their entirety.

FIELD OF THE INVENTION

The present invention relates to the use of centrally acting $NK_1$ antagonists to treat nausea and vomiting, particular nausea and vomiting induced by highly emetogenic chemotherapy, and to the treatment of such nausea and vomiting over multiple consecutive days. The present invention also relates to combined oral dosage forms of palonosetron and netupitant.

BACKGROUND OF THE INVENTION

With the development of the $5\text{-}HT_3$ antagonist in the early 1990s, there emerged new strategies in the medical community to better control nausea and vomiting caused by various medical procedures, including chemotherapy (CINV), surgery (PONV), and radiation therapy (RINV). When added to steroids such as dexamethasone, several $5\text{-}HT_3$ antagonists have been demonstrated to significantly improve the standard of life for patients undergoing emetogenic medical procedures. Examples of $5\text{-}HT_3$ antagonists include ondansetron, marketed by GlaxoSmithKline, and palonosetron, developed by Helsinn Healthcare.

Palonosetron hydrochloride has recently emerged as a highly efficacious anti-nauseant and anti-emetic agent. See PCT publications WO 2004/045615 and 2004/073714 from Helsinn Healthcare. Palonosetron hydrochloride is sold in the United States as a sterile injectable liquid under the ALOXI® brand, in sterile unit dose vials containing 0.075 or 0.25 mg. of palonosetron hydrochloride. Palonosetron hydrochloride also is also sold as an orally administered soft-gel dosage form containing 0.5 mg. of palonosetron hydrochloride.

The official chemical name for palonosetron hydrochloride is (3aS)-2-[(S)-1-Azabicyclo[2.2.2]oct-3-yl]-2,3,3a,4,5,6-hexahydro-1-oxo-1Hberiz[de]isoquinoline hydrochloride (CAS No. 119904-90-4); its empirical formula is $C_{19}H_{24}N_2O \cdot HCl$, and its molecular weight is 332.87. The compound is represented by the following chemical structure:

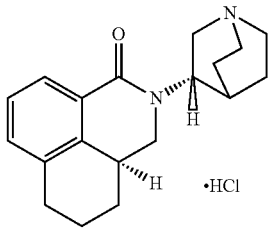 [SMILES: O=C1c2cccc3c2[C@H](CCC3)CN1[C@@H]1CN2CCC1CC2 ; Cl]

Methods of synthesizing palonosetron are described in U.S. Pat. Nos. 5,202,333 and 5,510,486. Pharmaceutically acceptably dosage forms are described in PCT publications WO 2004/067005 and WO 2008/049552 from Helsinn Healthcare.

$NK_1$ antagonists have also recently emerged as a tool for combating nausea and vomiting from emetogenic medical procedures. Most recently, aprepitant was approved by the Food and Drug Administration ("FDA") for use in combination with other anti-emetic agents for the prevention of nausea and vomiting from moderately and highly emetogenic chemotherapy. However, it quickly became apparent that aprepitant's effect was limited principally to vomiting—not nausea—and that aprepitant did not provide as much benefit during the acute phase of CINV. When tested against nausea in humans, aprepitant was unable to induce a significant reduction in the incidence or severity of nausea following moderately or highly emetogenic chemotherapy when compared to a $5\text{-}HT_3$ antagonist alone. See FDA Approved Labeling for Emend®. Thus, while aprepitant is approved by FDA for the prevention of nausea and vomiting in humans, this indication is somewhat misleading because aprepitant did not reduce nausea in the clinical trials preformed for aprepitant more than nausea controlled by the other components of the anti-emetic regimen. In addition, the results reported in Grunberg et al., Support Cancer Care (2009) 17:589-594, from a combined treatment of aprepitant and palonosetron, were far from promising.

Merck & Co. markets aprepitant, as EMEND® in the United States. The product is approved in a capsule dosage form, and is marketed for the prevention of CINV (acute and delayed) in combination with other anti-emetic agents such as ondansetron and metoclopramide. The product reportedly has a terminal half-life of from 9 to 13 hours. While aprepitant has demonstrated some effect against nausea, its effects have been inconsistent. Casopitant is another $NK_1$ antagonist that has been tested against nausea and vomiting in humans. A clinical study of casopitant is discussed in *Therapeutics and Clinical Risk Management* 2009:5 pp 375-384 to Ruhlmann et al. and *Drug Metabolism and Disposition*, vol. 37, No. 8, 2009, pp. 1635-1645 to Pellegatti et al. As reported by Ruhlmann et al. in Therapeutics and Clinical Risk Management, 2009:5 375-384, casopitant had no statistically significant effect against nausea when administered in response to moderately emetogenic chemotherapy, and even induced nausea as a side effect. Casopitant has the formula (2R,4S)-4-(4-acetytlpiperazin-1-yl)-N-{(1R)-1-[3,5-bis(trifluoromethyl) phenyl]ethyl}-2-(4-fluoro-2-methylphenyl)-N-methylpiperidine-1-carboxamide, and the below chemical structure:

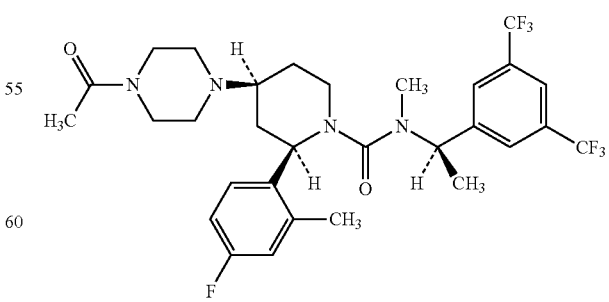

Netupitant is another selective $NK_1$ receptor antagonist under development by Helsinn Healthcare, having the formula 2-[3,5-bis(trifluoromethyl)phenyl]-N,2-dimethyl-N-

[4-(2-methylphenyl)-6-(4-methylpiperazin-1-yl)pyridin-3-yl]propanamide, or Benzeneacetamide, N,α,α-trimethyl-N-[4-(2-methylphenyl)-6-(4-methyl-1-piperazinyl)-3-pyridinyl]-3,5-bis(trifluoromethyl)-, and the below chemical structure:

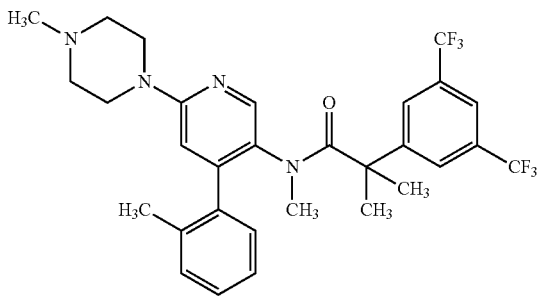 [SMILES: Cc1ccccc1-c1cc(N2CCN(C)CC2)ncc1N(C)C(=O)C(C)(C)c1cc(C(F)(F)F)cc(C(F)(F)F)c1]

Methods of synthesizing and formulating netupitant and its prodrugs are described in U.S. Pat. Nos. 6,297,375, 6,719,996 and 6,593,472 to Hoffmann La Roche.

Other representative $NK_1$ antagonists include ZD4974 (developed by AstraZeneca), CGP49823 (developed by Ciba-Geigy), Lanepitant and LY686017 (developed by Eli Lilly), FK888 (developed by Fujisawa), Vofopitant, Vestipitant and Orvepitant (developed by GlaxoSmithKline), Befetupitant (developed by Hoffmann-La Roche), R116031 (developed by Janssen), L-733060 and L-736281 (developed by Merck), TKA731, NKP608 and DNK333 (developed by Novartis), CP-96345, CP-99994, CP-122721, CJ-17493, CJ-11974 and CJ-11972 (developed by Pfizer), RP67580 and Dapitant (developed by Rhone-Poulenc Rorer), Nolpitantium and SSR240600 (developed by Sanofi-Aventis), SCH388714 and Rolapitant (developed by Schering-Plough), TAK637 (developed by Takeda), HSP117 (developed by Hisamitsu), KRP103 (developed by Kyorin Pharm) and SLV317 (developed by Solvay). Chemical structures of the above-mentioned $NK_1$ antagonists are shown below and discussion of those compounds as well as other $NK_1$ antagonists is present in *Expert Opin. Ther. Patents* (2010) 20(8), pp 1019-1045 by Huang et al.

The background of U.S. Pat. No. 6,297,375 suggests that $NK_1$ antagonists are useful for treating a variety of conditions in which substance P (the natural ligand for the $NK_1$ receptor) is active. These conditions include depression, pain (especially pain resulting from inflammatory conditions such as migraine, rheumatoid arthritis, asthma, and inflammatory bowel disease), central nervous system (CNS) disorders such as Parkinson's disease and Alzheimer's disease, headache, anxiety, multiple sclerosis, attenuation of morphine withdrawal, cardiovascular changes, oedema, chronic inflammatory diseases such as rheumatoid arthritis, asthma/bronchial hyperreactivity and other respiratory diseases including allergic rhinitis, inflammatory diseases of the gut including ulcerative colitis and Crohn's disease, ocular injury and ocular inflammatory diseases. The background even mentions motion sickness and vomiting, but fails to call out nausea specifically.

Accordingly, there is a need in the art for more effective treatments of nausea and vomiting, particularly nausea and vomiting emanating from chemotherapy, radiotherapy and surgery. In addition, given the prolonged incidence of nausea and vomiting induced by these emetic events, there is a need for treating such nausea and vomiting for a prolonged period of time. Further, there is a need for the development of dosage forms to reduce drug-drug interaction, improve stability, and potentiate effects of each component of the combined dosage forms.

OBJECTS OF THE INVENTION

Accordingly, it is an object of the invention to provide new methods for treating or preventing nausea and vomiting using an $NK_1$ antagonist, particularly netupitant.

It is another object of the invention to provide methods for treating or preventing nausea and vomiting in patients undergoing chemotherapy, radiotherapy, or surgery.

Still another object of the invention is to augment existing treatments for CINV, RINV or PONV by steroids and $5\text{-}HT_3$ antagonists, and thereby provide additional protection against both nausea and vomiting, especially during the acute and delayed phases.

Another object of the invention is to provide a single combined dose of netupitant and a $5\text{-}HT_3$ antagonist and to the use of that single dose without further dosing, for the treatment of nausea and vomiting during the acute and delayed phases of CINV, RINV or PONV.

It is another object to provide novel methods to treat nausea, vomiting, and other undesirable effects from moderately emetogenic and highly emetogenic chemotherapy ("MEC and HEC"), especially HEC, during the acute and delayed phases following such treatments.

It is another object to provide novel dosage forms to reduce drug-drug interaction, improve stability, enhance bioavailability and potentiate therapeutic effect of each component of the combined dosage forms comprising netupitant and/or $5\text{-}HT_3$ antagonist and/or dexamethasone, in treating or preventing nausea and vomiting.

SUMMARY OF THE INVENTION

After extensive testing into the clinical effects of netupitant, it has unexpectedly been discovered that netupitant is active against nausea, and that a single dose of netupitant is able to treat nausea and vomiting in response to highly and moderately emetogenic chemotherapy for five consecutive days. It has also been discovered, quite unexpectedly, that netupitant exhibits unique binding habits to $NK_1$ receptors in the brain. In particular, it has been discovered that netupitant binds to $NK_1$ receptors in the striatum in a long-lasting manner, and that less than 20 or 30% of netupitant is released from striatum $NK_1$ receptors even ninety-six hours after administration. This is in stark contrast to aprepitant, in which receptor binding drops swiftly over time, and must be dosed repeatedly if emesis control is desired throughout the delayed phase; and which shows no meaningful effect against nausea.

These discoveries have led to the development of a unique dosing regimen to treat nausea during the first day after an emesis-inducing event, in addition to the second, third, fourth and fifth days after such induction. Therefore, in one embodiment the invention provides a method of treating nausea and vomiting for a period of five consecutive days in a patient in need thereof, comprising administering to said patient netupitant or a pharmaceutically acceptable salt thereof in an amount which is therapeutically effective against nausea and vomiting during the acute and delayed phases, and which is effective to enter the systemic circulation, cross the blood brain barrier and occupy at least 70% of $NK_1$ receptors in the striatum seventy-two hours after said administration.

In another embodiment, the netupitant is combined with other anti-emetic agents, including a $5\text{-}HT_3$ antagonist such as palonosetron and a corticosteroid such as dexamethasone, in a manner that results in even greater efficacy against nausea. It has been discovered that palonosetron is much more effective in combinations with netupitant than it is in combination with aprepitant, as reported by Grunberg et al., Support Cancer Care (2009) 17:589-594. In addition, palonosetron shows an improved pharmacokinetic profile (e.g., better bioavailability) when palonosetron is in combination with netupitant as opposed to palonosetron in single dose administration. Based on these discoveries, solid oral dosage forms have been developed that combine netupitant or another NK1 antagonist and palonosetron for the treatment of acute and delayed emesis.

It has also been discovered that netupitant potentiates the effect of dexamethasone, such that the dexamethasone is effective even when administered at sub-therapeutic doses (i.e. doses at which the dexamethasone would be ineffective if administered by itself). Therefore, in another embodiment the invention provides a combination therapy for treating nausea and vomiting for five consecutive days in a patient in need thereof, consisting essentially of:

Day 1 netupitant—administering to said patient on day one netupinant or a pharmaceutically acceptable salt thereof, in an amount which is therapeutically effective against nausea and vomiting during the acute and delayed phases, and which is effective to enter the systemic circulation, cross the blood brain barrier and occupy at least 70% of $NK_1$ receptors in the striatum seventy-two hours after said administration;

Day 1 palonosetron—administering to said patient on day one a therapeutically effective amount of a $5-HT_3$ antagonist (preferably palonosetron) effective to treat said nausea and vomiting during the acute and delayed phases;

Day 1 dexamethasone—administering to said patient on day one a first dose of dexamethasone which is ineffective against nausea and vomiting when administered alone, but effective against nausea and vomiting when administered in combination with said netupitant and palonosetron, wherein said first dose comprises from 50 to 70% of a minimum effective dose when administered alone; and Days 2-5 dexamethasone—when the patient is undergoing highly emetogenic chemotherapy, administering to said patient, on days two, three and four, a second dose of dexamethasone which is ineffective against nausea and vomiting when administered alone, but effective against nausea and vomiting when administered in combination with said netupitant, wherein said second dose comprises from 40 to 60% of a minimum effective dose when administered alone on days two, three and four.

The dosage forms are extremely versatile and stable owing to their unique design and formulation. This versatility and stability is accomplished by formulating the NK1 antagonist and palonosetron in separate dosage forms and combining the dosage forms in one capsule. Thus, for example, the palonosetron can be formulated in a small gel-cap at a dose of around 0.5 mg, and the netupitant or other NK1 antagonist formulated in a tablet at a dose of about 100 to 150 mg. A capsule can then be filled with one or more palonosetron gel-caps and one or more netupitant (or other NK1 antagonist) tablets, depending on the therapeutic objective for the product. Because the palonosetron and NK1 antagonist are in separate dosage units, they can be formulated without regard to the stability of the other, and without degradation to by-products, for instance (3S)-3-[(3aS)-1-oxo-2,3,3a,4,5,6-hexahydro-1H-benzo[de]isoquinoline-2-yl]-1-azoniabicyclo[2.2.2]octan-1-olate, a degradation by-product of palonosetron. As a result, the presently discovered dosage forms offer advantages, such as, reducing drug-drug interaction, improving stability, and potentiating effects of each component of the dosage forms in treating or preventing emesis.

Thus, in one embodiment the invention provides an orally administered dosage form comprising a combination of palonosetron and an NK1 antagonist (preferably netupitant), or a pharmaceutically acceptable salt or prodrug thereof.

In another embodiment the invention provides an orally administered capsule dosage form comprising (a) an outer shell; (b) one or more tablets housed within said outer shell, each comprising an NK1 antagonist (preferably netupitant) or a pharmaceutically acceptable salt or prodrug thereof and one or more pharmaceutically acceptable excipients; and (c) one or more soft-gel capsules housed within the outer shell, each comprising palonosetron or a pharmaceutically acceptable ester or prodrug thereof and one or more pharmaceutically acceptable excipients; wherein said dosage form comprises (3S)-3-[(3aS)-1-oxo-2,3,3a,4,5,6-hexahydro-1H-benzo[de]isoquinoline-2-yl]-1-azoniabicyclo[2.2.2]octan-1-olate in an amount that does not exceed 3 wt. %.

In still other embodiments the invention provides methods of treating acute and delayed-onset emesis by administering the dosage forms of the present invention to a human in need thereof, preferably shortly before the emesis inducing event.

Additional embodiments and advantages of the invention will be set forth in part in the description which follows, and in part will be obvious from the description, or may be learned by practice of the invention. The embodiments and advantages of the invention will be realized and attained by means of the elements and combinations particularly pointed out in the appended claims. It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate several embodiments of the invention and together with the description, serve to explain the principles of the invention.

DETAILED DESCRIPTION OF THE INVENTION

Figure 1:
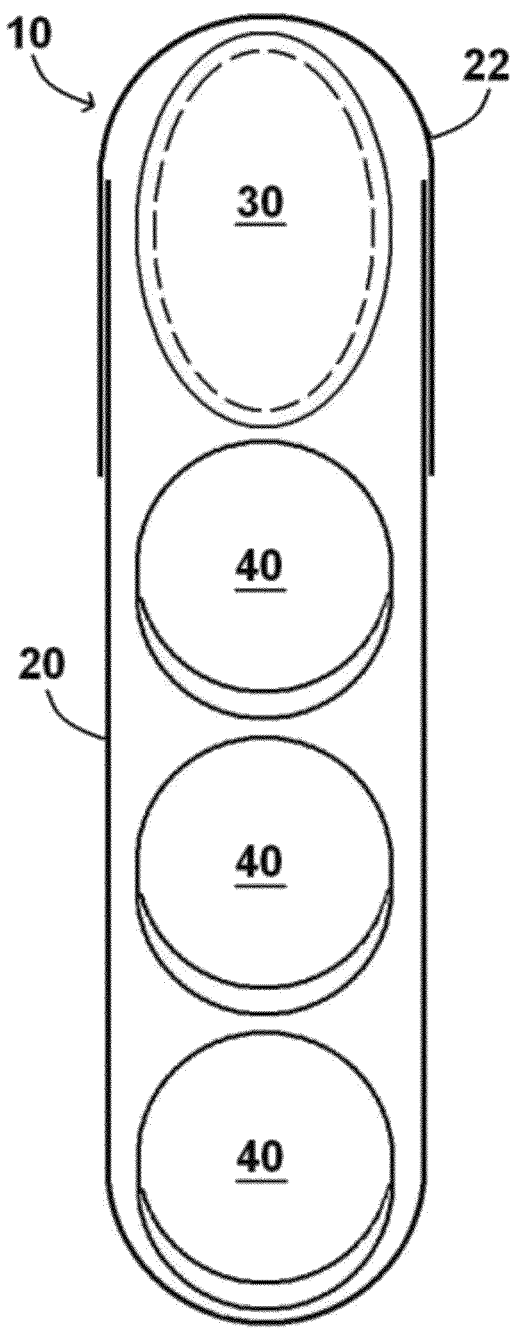
FIG. 1 depicts a capsule containing one soft-gel capsule of palonosetron and three tablets of netupitant.

The present invention may be understood more readily by reference to the following definitions and detailed description of preferred embodiments of the invention and the non-limiting Examples included therein.

Definitions and Use of Terms

When the singular forms "a," "an" and "the" or like terms are used herein, they will be understood to include plural referents unless the context clearly dictates otherwise. Thus, for example, reference to "a pharmaceutical carrier" includes mixtures of two or more such carriers, and the like. The word "or" or like terms as used herein means any one member of a particular list and also includes any combination of members of that list.

When used herein the term "about" or "ca." will compensate for variability allowed for in the pharmaceutical industry and inherent in pharmaceutical products, such as differences in product strength and bioavailability due to manufacturing variations and time-induced product degradation. The term allows for any variation which in the practice of pharmaceuticals would allow the product being evaluated to be considered pharmaceutically equivalent or bioequivalent, or both if the context requires, to the recited strength of a claimed product.

Throughout the description and claims of this specification, the word "comprise" and variations of the word, such as "comprising" and "comprises," means "including but not limited to," and is not intended to exclude, for example, other additives, components, integers or steps.

As used herein, the term "Pharmaceutically acceptable" means that which is useful in preparing a pharmaceutical composition that is generally safe, non-toxic and neither biologically nor otherwise undesirable and includes that which is acceptable for veterinary use as well as human pharmaceutical use. In addition, the term "pharmaceutically acceptable salt" refers to a salt of a compound to be administered prepared from pharmaceutically acceptable non-toxic acids. Examples of suitable inorganic acids are hydrochloric, hydrobromic, hydroiodic, nitric, sulfuric, and phosphoric. Suitable organic acids may be selected from aliphatic, aromatic, carboxylic and sulfonic classes of organic acids, examples of which are formic, acetic, propionic, succinic, camphorsulfonic, citric, fumaric, gluconic, isethionic, lactic, malic, mucic, tartaric, para-toluenesulfonic, glycolic, glucuronic, maleic, furoic, glutamic, benzoic, anthranilic, salicylic, phenylacetic, mandelic, embonic (pamoic), methanesulfonic, ethanesulfonic, pantothenic, benzenesulfonic (besylate), stearic, sulfanilic, alginic, galacturonic, and the like.

Pharmaceutically acceptable salts of palonosetron include palonosetron hydrochloride. Pharmaceutically acceptable pro-drugs of netupitant include those described in U.S. Pat. Nos. 6,593,472, 6,747,026 and 6,806,370, including the N-oxide of netupitant. The contents of these publications are incorporated herein by reference. When a molecule is referred to herein in its base or salt form, it will be understand also to encompass other pharmaceutically acceptable salt forms of the molecule.

As used herein, "therapeutically effective amount" refers to an amount sufficient to elicit the desired biological response. The therapeutically effective amount or dose will depend on the age, sex and weight of the patient, and the current medical condition of the patient. The skilled artisan will be able to determine appropriate dosages depending on these and other factors in addition to the present disclosure.

The minimum effective dose of dexamethasone, when used to treat CINV induced by highly emetogenic chemotherapy, has been demonstrated to be 20 mg. administered orally or by injection on day one, and sixteen mg. administered orally or by injection on days two, three and four. Jordan et al., THE ONCOLOGIST, Vol. 12, No. 9, 1143-1150, September 2007.

When used to treat CINV induced by moderately emetogenic chemotherapy, the minimum effective dose of dexamethasone is 20 mg. administered orally or by injection on day one, and zero mg. on days two, three and four.

The terms "treating" and "treatment," when used herein, refer to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

As used herein, the term "significantly" refers to a level of statistical significance. The level of statistical significant can be, for example, of at least $p<0.05$, of at least $p<0.01$, of at least $p<0.005$, or of at least $p<0.001$. Unless otherwise specified, the level of statistical significance is $p<0.05$. When a measurable result or effect is expressed or identified herein, it will be understood that the result or effect is evaluated based upon its statistical significance relative to a baseline. In like manner, when a treatment is described herein, it will be understood that the treatment shows efficacy to a degree of statistical significance.

5-$HT_3$ antagonists include the various setrons such as, for example, palonosetron, ondansetron, dolasetron, tropisetron, and granisetron, and their pharmaceutically acceptable salts. A preferred 5-$HT_3$ antagonist is palonosetron, especially its hydrochloride salt.

"Highly emetogenic chemotherapy" refers to chemotherapy having a high degree of emetogenic potential, and includes chemotherapy based on carmustine, cisplatin, cyclophosphamide≥1500 mg/$m^2$, dacarbazine, dactinomycin, mechlorethamine, and streptozotocin.

"Moderately emetogenic chemotherapy" refers to chemotherapy having a moderate degree of emetogenic potential, and includes chemotherapy based on carboplatin, cyclophosphamide<1500 mg/$m^2$, cytarabine>1 mg/$m^2$, daunorubicin, doxorubicin, epirubicin, idarubicin, ifosfamide, irinotecan, and oxaliplatin.

Acute emesis refers to the first twenty-four hour period following an emesis-inducing event. Delayed emesis refers to the second, third, fourth and fifth twenty-four hour periods following an emesis-inducing event. When a treatment is said to be effective during the delayed phase, it will be understood to mean that the effectiveness of the treatment is statistically significant during the entire delayed phase, regardless of whether the treatment is effective during any particular twenty-four hour period of the delayed phase. It will also be understood that the method can be defined based upon its effectiveness during any one of the twenty-four hour periods of the delayed phase. Thus, unless otherwise specified, any of the methods of treating nausea and/or vomiting during the delayed phases, as described herein, could also be practiced to treat nausea and/or vomiting during the second, third, fourth or fifth twenty-four hour periods following an emesis inducing event, or an combination thereof.

When ranges are given by specifying the lower end of a range separately from the upper end of the range, it will be understood that the range can be defined by selectively combining any one of the lower end variables with any one of the upper end variables that is mathematically possible.

Methods of Treatment

As noted above, the invention is premised on several unique discoveries, and provides the following independent methods that can be practiced according to the present invention, including:

In a first principal embodiment, the invention provides a method of treating nausea and vomiting for a period of five consecutive days in a patient in need thereof, comprising administering to said patient netupitant or a pharmaceutically acceptable salt thereof in an amount which is therapeutically effective to treat nausea and vomiting during the acute and delayed phases, which enters the systemic circulation, crosses the blood brain barrier and occupies at least 70% of $NK_1$ receptors in the striatum seventy-two hours after said administration.

In a second principal embodiment, the invention provides a combination therapy for treating nausea and vomiting for five consecutive days in a patient in need thereof, comprising:

(i) administering to said patient on day one netupitant or a pharmaceutically acceptable salt thereof, in an amount which is therapeutically effective to treat nausea and vomiting during the acute and delayed phases, which enters the systemic circulation, crosses the blood brain barrier and occupies at least 70% of $NK_1$ receptors in the striatum seventy-two hours after said administration;

(ii) administering to said patient on day one a therapeutically effective amount of a $5-HT_3$ antagonist (preferably palonosetron, more preferably 0.5 mg. of oral palonosetron as palonosetron hydrochloride) effective to treat said nausea and vomiting during the acute and delayed phases;

(iii) administering to said patient on day one a first dose of dexamethasone which is ineffective against nausea and vomiting when administered alone, but effective against nausea and vomiting when administered in combination with said netupitant and palonosetron, wherein said first dose comprises from 50 to 70% of a minimum effective dose when administered alone; and (iv) if the patient is undergoing highly emetogenic chemotherapy, administering to said patient, on days two, three and four, a second dose of dexamethasone which is ineffective against nausea and vomiting when administered alone, but effective against nausea and vomiting when administered in combination with said netupitant, wherein said second dose comprises from 40 to 60% of a minimum effective dose when administered alone on days two, three and four.

Various sub-embodiments are envisaged for these principal embodiments. For example, the netupitant can be administered as a free base or a pharmaceutically acceptable salt thereof, but is preferably administered as the free base. In addition, the netupitant is preferably administered in an amount ranging from about 50 to about 500 mg., from about 200 to about 400 mg., and preferably about 300 mg., based on the weight of the free base. A preferred route of administration for the netupitant is oral. In terms of binding to $NK_1$ receptors, the netupitant preferably binds to at least 80 or even 85% of $NK_1$ receptors in the striatum seventy-two hours after administration. As of ninety six hours after administration, the netupitant preferably binds less than 70, 60, 50 or even 40% of said $NK_1$ receptors.

The methods of the present invention are all effective at treating or preventing nausea and vomiting induced by numerous events, including chemotherapy induced nausea and vomiting ("CINV"), from moderately or highly emetogenic chemotherapy, radiation therapy induced nausea and vomiting ("RINV"), and post-operative nausea and vomiting ("PONV"). The method is preferably performed shortly before the emesis inducing event (i.e. no more than 1 or 2 hours before the event). The methods may be used to treat nausea and vomiting during the acute phase of emesis, or during the delayed phase.

The drugs specified by the individual embodiments may be administered by any suitable dosing regimen, as is well known in the art, but in a preferred embodiment the netupitant, $5-HT_3$ antagonist and steroid are administered orally. A preferred oral dose of palonosetron ranges from about 0.075 to about 1.0 mg, or from about 0.25 to about 0.75 mg, but is preferably about 0.5 mg. A preferred oral dose of netupitant ranges from about 50 to 500 mg, or from about 200 to about 400 mg, but is preferably about 300 mg. A preferred dose of corticosteroid, preferably dexamethasone, is 12 mg administered orally or via injection on the first day of treatment, and 8 mg administered orally or via injection on the second, third and fourth days after said treatment.

It will be further understood that the netupitant can be administered in prodrug form, in which case the invention will provide a method of treatment by inducing plasma levels of netupitant, and in each case the plasma level of netupitant induced by the prodrug administration will correspond to the level attained by the administration of netupitant or its pharmaceutically acceptable salt, in the doses and routes of administration described herein.

Pharmaceutical Compositions

Various pharmaceutical compositions can be developed that make use of the combinations described herein. The composition can be administered by any appropriate route, for example, orally, parenterally, or intravenously, in liquid or solid form.

Preferred modes of administrations of the active compounds are injectable and/or oral. These compositions will generally include an inert diluent or an edible carrier. They may be enclosed in gelatin capsules (for oral use) or compressed into tablets (for oral or buccal use) or formulated into troches (for buccal use). For these purposes, the active compound can be incorporated with excipients and used in the form of tablets, troches, or capsules. Pharmaceutically compatible binding agents, and/or adjuvant materials can be included as part of the composition.

Tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a gliding such as colloidal silicon dioxide; a sweetening agent such as sucrose or saccharin; or a flavoring agent such as peppermint, methyl salicylate, or orange flavoring. When the dosage unit form is a capsule, it can contain, in addition to material of the above type, a liquid carrier such as a fatty oil. In addition, dosage unit forms can contain various other materials which modify the physical form of the dosage unit, for example, coatings of sugar, shellac, or other enteric agents.

The compounds can be administered as a component of an elixir, suspension, syrup, wafer, orally disintegrating film, orally disintegrating tablet, chewing gum or the like. A syrup may contain, in addition to the active compounds, sucrose as a sweetening agent and certain preservatives, dyes and colorings and flavors.

Solutions or suspensions used for injection can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride, mannitol and dextrose. An injectable preparation can be enclosed in ampoules, disposable syringes or multiple dose vials made of glass or plastic.

Combined Oral Dosage Forms

As discussed above, the invention provides versatile combined oral dosage forms of palonosetron and an NK1 antagonist that can be readily modified depending on the therapeutic objective, and that do not present issues of stability and degradation. In a preferred embodiment, the invention provides a capsule for oral administration made from a hard outer shell that houses one or more NK1 antagonist tablets and one or more palonosetron soft-gel capsules. The finished capsule and the tablet(s) and soft-gel capsule(s) housed within the capsule shell are all preferably formulated as immediate release dosage forms. Netupitant and casopitant, and their pharmaceutically acceptable salts, are particularly preferred NK1 antagonists for the combined oral dosage forms of this invention.

While the NK1 antagonist is preferably formulated in a solid tablet, it will be understood that it can be formulated in any solid form that is suitable for oral administration including, for example, a tablet or capsule (hard or soft-gel). In a preferred embodiment, the NK1 antagonist is formulated in a tablet. The number of NK1 antagonist units contained within the combined dosage form can be, for example, from 1 to 10, 1 to 5, or 1 to 3. The netupitant units within the combined dosage form can provide anywhere from 50 to 500 mg of netupitant on an aggregate basis, preferably from 100 to 350 mg. Each netupitant unit preferably comprises from 50 to 200 mg of netupitant, more preferably 100 to 150 mg of netupitant, and most preferably 100 or 150 mg of netupitant.

The palonosetron can also be formulated in any solid form that is suitable for oral administration, although it is preferably formulated as a soft-gel capsule. Non-limiting examples of suitable palonosetron soft-gel capsules are provided in PCT publication WO 2008/049552, the contents of which are hereby incorporated by reference. The number of palonosetron units within the combined dosage form can be, for example, from 1 to 5, from 1 to 3 or just 1. Each of the palonosetron units within the combined dosage form can provide anywhere from 0.01 to 5.0 mg palonosetron, preferably from 0.1 to 1.0 mg palonosetron on an aggregate basis. Each palonosetron unit will preferably comprise from 0.1 to 1.0 mg of palonosetron, most preferably about 0.25, 0.5, 0.75 or 1.0 mg of palonosetron.

FIG. 1 illustrates an exemplary embodiment of a combined oral dosage form of palonosetron and netupitant. The dosage form 10 comprises a two piece hard outer shell that includes a body 20 and a cap 22. The dosage form 10 contains one palonosetron soft-gel capsule 30 (preferably containing 0.5 mg of palonosetron) and three netupitant tablets 40 (each preferably containing 100 mg of netupitant).

Hard Outer Shell

The hard outer shell of the present invention can be made of any pharmaceutically acceptable material that dissolves in gastric fluids. Preferred materials for the hard outer shell include, for example, gelatin, cellulose, starch, or hydroxypropyl methylcellulose (HPMC). In a particular embodiment of the invention, the hard outer shell has a maximum oxygen permeability. Preferably, the oxygen permeability is less about $1.0\times10^{-3}$, $5.0\times10^{-4}$, $1.0\times10^{-4}$, $5.0\times10^{-5}$, or even $2.0\times10^{-5}$ ml·cm/(cm$^2$·24 hr. atm).

The hard outer shell can be a continuous structure. Alternatively, the hard outer shell can be a two-piece hard capsule.

Soft-Gel Capsule

The soft-gel capsule used for the palonosetron preferably comprises a soft outer shell and a liquid inner fill composition comprising palonosetron hydrochloride. Non-limiting examples of suitable palonosetron soft-gel capsules are provided in PCT publication WO 2008/049552, the contents of which are hereby incorporated by reference.

The soft outer shell of the soft-gel capsule can contain any type of material that dissolves in gastric fluids. Preferred materials for the soft outer shell include, for example, gelatin, cellulose, starch, or hydroxypropyl methylcellulose (HPMC). The soft-gel capsule can further comprise shell excipients such as glycerin, sorbitol, and colorants/opacifers such as titanium dioxide. The soft-gel capsule can further include solvents such as purified water. In particular embodiments of the invention, the outer shell has a maximum oxygen permeability, preferably of no more than $1.0\times10^{-3}$, $5.0\times10^{-4}$, $1.0\times10^{-4}$, $5.0\times10^{-5}$, or even $2.0\times10^{-5}$ ml·cm/(cm$^2$·24 hr. atm). Suitable soft-gel capsules include the 1.5-oval gelatine capsule shell manufactured by Catalent Pharma Solutions.

The liquid fill is preferably composed predominantly of one or more lipophilic components in an amount of from 50 wt. % to 99 wt. %, preferably from 75 wt. % to 98 wt. %. Preferred lipophilic components include, for example, mono- and di-glycerides of fatty acids, especially including the mono- and di-glycerides of capryl/capric acid. The liquid fill may also contain glycerin, preferably in an amount of from 1 to 15 wt. %, more preferably from 2 to 10 wt. %. In one preferred embodiment, both the shell and the inner fill composition comprise glycerin. In another preferred embodiment, the liquid fill comprises about 0.25, 0.50, 0.75 mg., or more of palonosetron as palonosetron hydrochloride.

The fill composition may comprise various means to facilitate the transition of palonosetron from the dosage form to the gastrointestinal fluids of the GI tract, so that the palonosetron may be more readily absorbed into the bloodstream. For example, the liquid fill composition may contain a surfactant, optimally in an amount of from 0.1 wt. % to 6 wt. %, from 0.5 wt. % to 5 wt. %, or from 1.0 wt. % to 3.0 wt. %. The liquid fill composition preferably comprises greater than 0.1, 0.5, or 1.0 wt. % of surfactant, and less than 10, 8, 5, 4, or even 4 wt. % of surfactant. A particularly preferred surfactant is polyglyceryl oleate.

Alternatively or in addition, the transitioning means for a liquid filled capsule may comprise water that forms a single phase or microemulsion with the other liquid ingredients in the excipient base. The liquid fill composition preferably comprises from 0.05 wt. % to 30 wt. % water, from 1 wt. % to 20 wt. % water, or from 2 wt. % to 10 wt. % water. The liquid fill preferably comprises greater than 0.1, 0.5 or 1.0 wt. % water, and less than 20, 15, 10, 8 or 5 wt. % water.

The active agent, which is preferably palonosetron hydrochloride, is preferably present in the fill composition in an amount ranging from 0.01 to 10.0 wt. %, from 0.05 to 5.0 wt. %, or from 0.1 wt. % to 2.0 wt. %. Alternatively, particularly stable formulations have been found where the concentration of palonosetron exceeds 0.3%, preferably at a concentration no greater than 1 wt. %.

Tablet

The tablets of the present invention can include from 20 to 95 wt. % of NK1 antagonist (preferably netupitant), and preferably comprises from 60 to 80 wt. % of netupitant. In addition, the tablets can contain diluents, disintegrants, surfactants, binders, glidants, and/or lubricants. In a particular embodiment, the tablet comprises from 5 to 25 wt. % of microcrystalline cellulose. The microcrystalline cellulose can function as a diluent and disintegrant, and preferably comprises 15 wt. % of the tablet. Another suitable disintegrant is sodium croscaramellose, which can be present in the tablet in an amount of from 1 to 5 wt. %, preferably 2 wt. %.

A suitable binder for use in the tablet is polyvinylpyrrolidone, which can be present in the tablet in an amount from 1 to 10 wt. % of the tablet, and preferably 5 wt. %. A suitable glidant for use in the tablet is colloidal silicon dioxide, which can be present in the tablet in an amount of 2 wt. %. Suitable lubricants for use in the tablet include sodium stearyl fumarate and magnesium stearate, which can be present in the tablet in an amount of 0.7 wt. % and 0.35 wt. %, respectively.

Application of the Combined Oral Dosage Forms

The invention further provides a method of treating emesis comprising orally administering to a patient suffering from emesis, or at risk for suffering emesis, a dosage form of the present invention. In still further embodiments, the invention provides methods of treating emesis by administering one or more of the dosage forms described herein. The dosage form is preferably administered shortly before the emesis inducing event (i.e. no more than 2 hours before the event). The emesis may be acute phase emesis (i.e. emesis experienced within about 24 hours of an emesis inducing event), or delayed emesis (i.e. emesis experienced after the acute phase, but within seven, six, five or four days of an emesis inducing event). The emesis may constitute chemotherapy induced nausea and vomiting ("CINV"), from moderately or highly emetogenic chemotherapy, radiation therapy induced nausea and vomiting ("RINV"), or post-operative nausea and vomiting ("PONV").

EXAMPLES

The following examples are put forth so as to provide those of ordinary skill in the art with a complete disclosure and description of how the compounds claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.) but some errors and deviations should be accounted for. Unless indicated otherwise, parts are parts by weight, temperature is in ° C. or is at room temperature, and pressure is at or near atmospheric.

Example 1

Preparation of Oral Dosage Form

In a preferred embodiment the combination is administered in a capsule oral dosage form, wherein the capsule houses one or more soft-gel capsules for the palonosetron and one or more hard tablets for the netupitant. Table 1 below describes a representative formulation for a soft-gel capsule containing 0.5 mg of palonosetron, suitable for inclusion in such a hard outer shell.

TABLE 1

REPRESENTATIVE SOFT-GEL FORMULATION

| Ingredient | Approximate Amount (mg/Capsule) | Function |
| --- | --- | --- |
| Fill Solution | | |
| Palonosetron HCl | 0.56[1] | Active |
| Mono- and di-glycerides of Capryl/Capric Acid (Capmul MCM) | 62.19 | Solvent vehicle |
| Glycerin, anhydrous, USP/Ph Eur | 3.37 | Plasticizer |
| Polyglyceryl oleate (Plurol Oleique CC 497) | 0.87 | Surfactant |
| Purified water, USP/Ph Eur | 2.94 | Co-solvent |
| Butylated hydroxyanisole (BHA), NF/Ph Eur | 0.07 | Antioxidant |
| Nitrogen | — | |
| Theoretical fill weight | 70.00 mg | |
| Gelatine Capsule Shell, 1.5-oval (Catalent Pharma Solutions)[2] | | |
| Gelatine (type 195), NF/Ph Eur | — | Shell |
| Sorbitol Special/Glycerin Blend 50/50 | — | Plasticizer |
| Titanium dioxide, USP/Ph Eur | — | Colorant/Opacifier |
| Purified water, USP/Ph Eur | — | Solvent |

[1]Corresponds to 0.50 mg. free base
[2]Quantitative composition of capsule shell is proprietary to Catalent Pharma Solutions Table 2 below describes a representative formulation for a tablet containing 100 mg. of netupitant, suitable for inclusion in a hard shell.

TABLE 2

REPRESENTATIVE TABLET FORMULATION

| Ingredient | Approximate Amount (mg/Tablet) | Function |
| --- | --- | --- |
| Netupitant, milled | 100 | Active |
| Microcrystalline cellulose pH 101 | 20.5 | Diluent and disintegrant |
| Sucrose Lauric Acid Esters | 10.0 | Surfactant |
| Polyvinilpyrrolidone K30 | 7.0 | Binder |
| Sodium croscaramellose | 3.0 | Disintegrant |
| Colloidal Silicon Dioxide | 3.0 | Glidant |
| Sodium Stearyl Fumarate | 1.0 | Lubricant |
| Magnesium Stearate | 0.5 | Lubricant |
| Total weight | 145 mg | |

Example 2

Pharmacokinetics of Combind Dosage Form

Objective

The effects of palonosetron on the pharmacokinetics (PK) of netupitant and the effects of netupitant on the PK of palonosetron were examined in healthy volunteers.

Methods

A randomized, open, 3-way crossover study was conducted. Each subject participated in 3 treatment periods, each lasting approximately 12 days (Day −1 to Day 11). The treatment periods were separated by wash-out periods of no less than 14 days (between Day 1 of any 2 consecutive treatment periods).

The following treatments were investigated:

Treatment A: oral netupitant 450 mg. administered as single dose of three 150 mg. capsules.

Treatment B: oral palonosetron 0.75 mg. and oral netupitant 450 mg. administered simultaneously as three capsules of 150 mg. netupitant followed by 1 capsule of 0.75 mg. palonosetron.

Treatment C: oral palonosetron 0.75 mg. administered as single dose as one 0.75 mg. capsule.

Doses were administered under fasting conditions. Subjects fasted over-night for approximately 10 hours. Water, however, was permitted up to 1 hour pre-dose. Food intake was permitted 4 hours post-dose, and water was allowed ad libitum 1 hour post-dose.

Doses were administered with the subject in an upright position. The subjects remained in an upright position for 4 hours post-dose. The capsules were swallowed whole with 250 mL of room-temperature tap water. Repeated PK blood sampling (for netupitant and/or palonosetron) was performed.

Results

Figure 2:
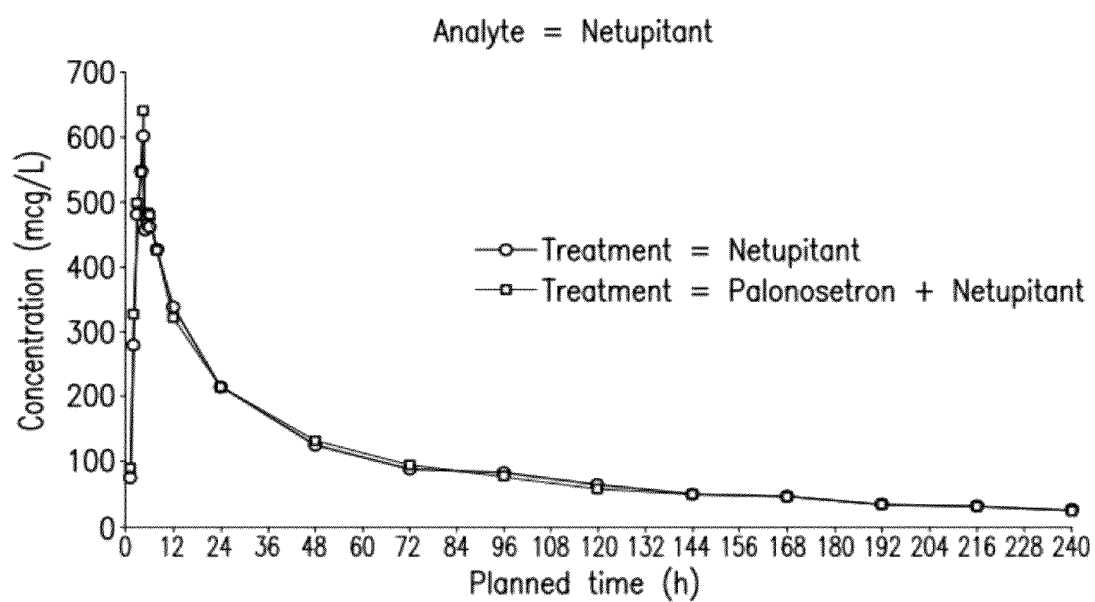
FIG. 2 is a two dimensional graph plotting the pharmacokinetic profile of netupitant in humans following oral administration of netupitant alone and netupitant together with palonosetron.
Figure 3:
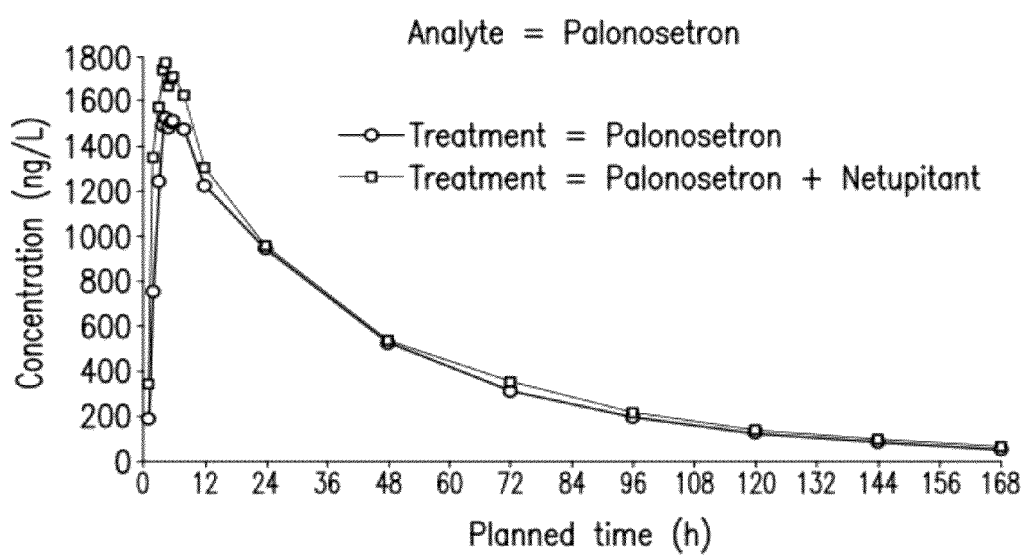
FIG. 3 is a two dimensional graph plotting the pharmacokinetic profile of palonosetron in humans following oral administration of palonosetron alone and palonosetron together with netupitant.

The primary PK variables assessed for netupitant and palonosetron were the maximum plasma concentration observed ($C_{max}$), the area under the plasma concentration versus time curve from time zero to the last quantifiable sampling time point (t) ($AUC_{0-t}$), and the area under the plasma concentration versus time curve from time zero to infinity ($AUC_{0-inf}$). The secondary PK variables assessed were the terminal elimination half-life ($t_{1/2,z}$), and the time at which the maximum plasma concentration was observed ($t_{max}$). Results are depicted in below Tables 3 and 4, as well as FIGS. 2 and 3.

TABLE 3

Summary of Netupitant Pharmacokinetic Parameters

| Parameter | Netupitant 450 mg | Palonosetron 0.75 mg + Netupitant 450 mg |
|---|---|---|
| $AUC_{0-t}$ [h * μg/L] | 22808 (7270) | 22775 (10064) |
| $AUC_{0-inf}$ [h * μg/L] | 25927 (10156) | 26241 (13219) |
| $C_{max}$ [μg/L] | 650.2 (257.8) | 659.7 (325.7) |
| $t_{max}$ (h) | 4.50 (3.00; 24.00) | 4.50 (3.00; 23.95) |
| $t_{1/2,z}$ (h) | 71.81 (37.10; 261.61) | 78.31 (50.17; 196.13) |

Mean and SD are shown, except for $t_{max}$ and $t_{1/2}$, where median and range are shown.

As can be seen in Table 4 below, palonosetron shows a better pharmacokinetic profile when combined with Netupitant as opposed to administered as a single dose of palonosetron, for example, the greater AUC, the larger $C_{max}$, the shorter $t_{max}$ (the median $t_{max}$ was 0.5 hour shorter after administration of palonosetron in combination with netupitant), and the longer $t_{1/2,z}$.

TABLE 4

Summary of Palonosetron Pharmacokinetic Parameters

| Parameter | Palonosetron 0.75 mg | Palonosetron 0.75 mg + Netupitant 450 mg |
|---|---|---|
| $AUC_{0-t}$ [h * μg/L] | 67415 (19554) | 74230 (24866) |
| $AUC_{0-inf}$ [h * μg/L] | 70813 (20415) | 77254 (25402) |
| $C_{max}$ [μg/L] | 1638.4 (415.5) | 1863.1 (487.1) |
| $t_{max}$ (h) | 5.02 (4.00; 8.00) | 4.50 (3.00; 6.02) |
| $t_{1/2,z}$ (h) | 34.73 (19.61; 70.46) | 36.91 (20.23; 56.08) |

Mean and SD are shown, except for $t_{max}$ and $t_{1/2}$, where median and range are shown.

Example 3

Netupitant+Dexamethasone Drug Interaction Study

The effect of netupitant on orally administered dexamethasone pharmacokinetics was evaluated in this study. This was a randomized, open, 3-period crossover study utilizing an incomplete Latin Square design where subjects were given dexamethasone alone, or oral Netupitant 100 mg., 300 mg. or 450 mg. each given with dexamethasone. Netupitant was given orally on Day 1 only. The dexamethasone regimen for each treatment was 20 mg. orally Day 1, followed by 8 mg. orally every 12 hours from Day 2 through Day 4. Nineteen subjects (12 male and 7 female) completed the study (i.e., all 3 treatment periods).

Figure 4:
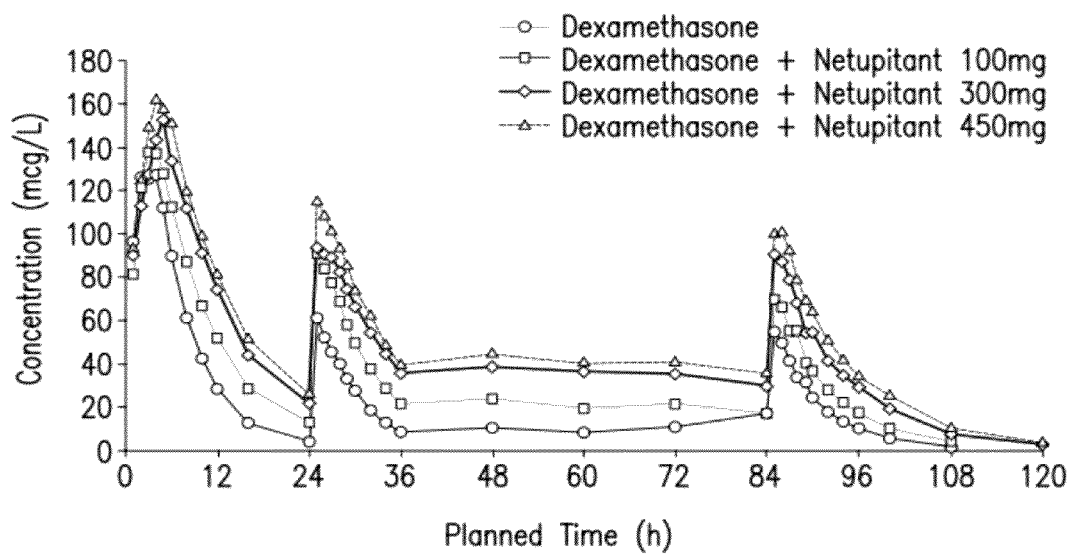
FIG. 4 is a two dimensional graph plotting mean plasma concentrations of dexamethasone over time following administration with and without netupitant.

Mean plasma concentrations of dexamethasone were higher when dexamethasone was co-administered with netupitant (FIG. 4). The increase appeared to be dependant on the netupitant exposure.

The $AUC_{0-24}$ (Day 1) of dexamethasone increased 1.5, 1.7 and 1.8-fold with co-administration of 100, 300 and 450 mg. netupitant, respectively. The $AUC_{24-36}$ (Day 2) of dexamethasone increased 2.1, 2.4 and 2.6-fold and $AUC_{84-108}$ and $AUC_{84-inf}$ (Day 4) increased 1.7, 2.4 and 2.7-fold, with co-administration of 100, 300 and 450 mg. netupitant, respectively. Dexamethasone $C_{max}$ on Day 1 was only slightly affected by co-administration of netupitant (1.1-fold increase during co-administration with 100 and 300 mg. netupitant, respectively, and 1.2-fold increase during co-administration with 450 mg. netupitant). $C_{max}$ on Day 2 and Day 4 was increased approximately 1.7-fold in subjects administered netupitant. Dexamethasone $C_{min}$ on Days 2-4 was increased approximately 2.8, 4.3 and 4.6-fold with co-administration of 100, 300 and 450 mg. netupitant, respectively. This clearly shows that the co-administration of netupitant and dexamethasone enhances the bioavailability of dexamethasone and provides a better therapeutic window of dexamethasone.

Example 4

Netupitant Pet Receptor Occupancy Study

This was a randomized, open-label, positron emission tomography (PET) study using 11C-GR205171 as tracer in 6 healthy male volunteers (2 per dose level) receiving single doses of netupitant (100, 300 or 450 mg) to investigate the degree of occupancy of $NK_1$ receptors in human brain, and to determine the relationship between plasma concentration of netupitant and $NK_1$ receptor occupancy (RO).

The anticipated high $NK_1$-RO (90% or higher) close to the expected $C_{max}$ (6 hours post dose) was reached for striatum, occipital cortex, frontal cortex and anterior cingulate in 3 of 6 subjects of whom 1 received 300 mg. and 2 received 450 mg. of netupitant as a single oral dose.

Figure 5:
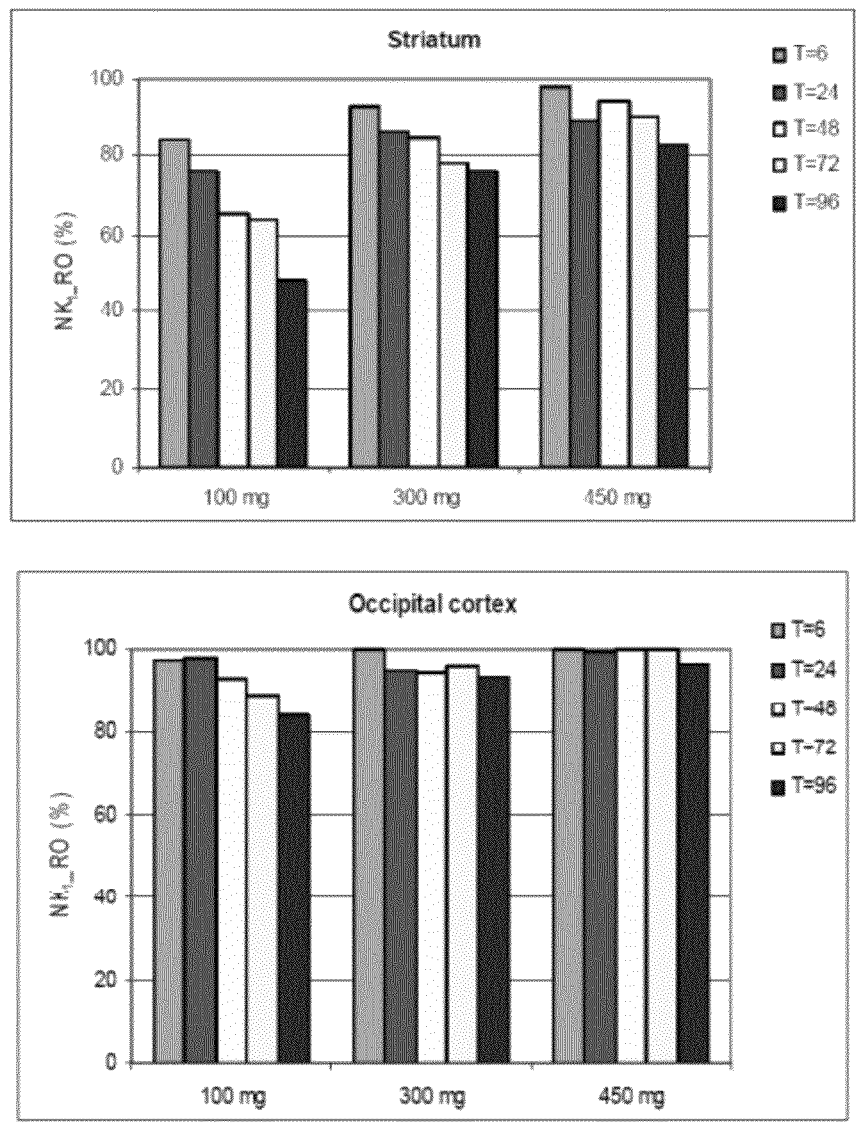
FIG. 5 contains two bar graphs that depict the average $NK_1$ receptor occupancy at 6, 24, 48, 72 and 96 hours after a single oral dose of 100, 300 and 450 mg. netupitant (N=2 for each dose) in striatum and occipital cortex, as measured using positron emission topography.

All doses showed a relatively long duration of blockade of $NK_1$ receptors and the decline over time was dose dependent. In the 100 mg. dose group, 4 of 6 regions still had a mean $NK_1$-RO over 70% at 96 hours post dose. In the highest dose group (450 mg), 5 of 6 regions had a mean $NK_1$-RO of 80% or higher at 96 hours post dose. A comparison of the results for the dose groups (100 mg., 300 mg. and 450 mg) showed a consistent but small increase in $NK_1$-ROs with increasing netupitant dose. (FIG. 5)

Example 5

Clinical Efficacy Study

A phase 2 trial evaluated three single doses of netupitant combined with palonosetron and dexamethasone compared to palonosetron alone and dexamethasone to obtain dose ranging information for netupitant used with oral palonosetron in the CINV patient population.

The objective of the study was to compare the efficacy and safety of three single oral doses of netupitant combined with oral palonosetron and given with dexamethasone, versus oral palonosetron-alone given with dexamethasone (without netupitant) for the prevention of highly emetogenic chemotherapy (HEC)-induced nausea and vomiting. The FDA-approved oral aprepitant regimen given with IV ondansetron and dexamethasone was included in the study as an active comparator for exploratory purposes. The FDA-approved oral palonosetron 0.5 mg. dose was used in each applicable treatment group in this study.

This was a multicenter, randomized, double-blind, double-dummy, parallel group, stratified study. Eligible patients were randomized (stratified by gender) to one of the following treatment groups:

Group 1—0.5 mg. oral palonosetron on Day 1 (with an oral dexamethasone standard regimen: 20 mg. on Day 1 and 8 mg. BID from Day 2 through Day 4)

Group 2—100 mg. oral netupitant plus 0.5 mg. oral palonosetron on Day 1 (with an oral dexamethasone adjusted regimen*: 12 mg. on Day 1 and 8 mg. daily from Day 2 through Day 4)

Group 3—200 mg. oral netupitant plus 0.5 mg. oral palonosetron on Day 1 (with an oral dexamethasone adjusted regimen*: 12 mg. on Day 1 and 8 mg. daily from Day 2 to Day 4)

Group 4—300 mg. oral netupitant plus 0.5 mg. oral palonosetron on Day 1 (with dexamethasone adjusted regimen*: 12 mg. on Day 1 and 8 mg. daily from Day 2 to Day 4)

Group 5—125 mg. oral aprepitant plus IV ondansetron 32 mg. (both on Day 1) then 80 mg. oral aprepitant on Day 2 and Day 3, (all with an oral dexamethasone adjusted regimen: 12 mg. on Day 1 and 8 mg. daily from Day 2 through Day 4)

In addition, a Group 6 was added to the analysis for comparative purposes, based on the results reported by Grunberg et al., Support Cancer Care (2009) 17:589-594:

Group 6—285 mg. oral aprepitant plus 20 mg. oral dexamethasone plus 0.2 mg. palonosetron i.v. (all on Day 1) then 80 mg. oral aprepitant The primary efficacy endpoint was the complete response rate (defined as no emetic episodes, no rescue medication) within 120 hours after the start of the highly emetogenic chemotherapy administration. Secondary efficacy endpoints were:

Complete response for the 0-24 hour interval (acute phase); and for the 25-120 hour interval (delayed phase);

Complete protection (defined as no emesis, no rescue therapy, no significant nausea); Total control (defined as no emesis, no rescue therapy and no nausea); No nausea (maximum VAS<5 mm); No significant nausea (maximum VAS<25 mm); No rescue medication; No emesis. These endpoints were evaluated for the 0-120 hour interval (overall), acute and delayed phase.

Time to first emetic episode, Time to first rescue medication, Time to treatment failure (based on time to the first emetic episode or time to the first rescue medication, whichever occurs first);

Severity of nausea for the overall, acute and delayed phase; Patient global satisfaction with anti-emetic therapy by means of VAS for each 24 hour interval.

Complete response rates are summarized in Table 5. The percent of patients with complete response over 0-120 hours after start of cisplatin administration was 76.5% in the palonosetron alone group and 87.4%, 87.6%, and 89.6% in the netupitant 100 mg., 200 mg., and 300 mg. groups, respectively. Differences from palonosetron-alone were greater than 10% (10.9% to 13.2%). All doses of netupitant were statistically superior to palonosetron alone (p-value=0.004 for the netupitant 300 mg. combination group).

TABLE 5

COMPLETE RESPONSE RATE FOR THE OVERALL, ACUTE AND DELAYED PHASE: MFAS Population

| Efficacy endpoint | Palo alone (n = 136) | Palo + Netu 100 mg (n = 135) | Palo + Netu 200 mg (n = 137) | Palo + Netu 300 mg (n = 135) | Aprepitant Regimen (N = 134) |
|---|---|---|---|---|---|
| CR, Overall Phase, 0-120 h | | | | | |
| Percent of Patients | 76.5 | 87.4 | 87.6 | 89.6 | 86.6 |
| Difference from Palo alone (%) | | 10.9 | 11.1 | 13.2 | 10.1 |
| p-value (*) | | 0.018 | 0.017 | 0.004 | 0.027 |
| CR, Acute Phase, 0-24 h | | | | | |
| Percent of Patients | 89.7 | 93.3 | 92.7 | 98.5 | 94.8 |
| Difference from Palo alone (%) | | 3.6 | 3.0 | 8.8 | 5.1 |
| p-value (*) | | 0.278 | 0.383 | 0.007 | 0.114 |
| CR, Delayed Phase, 25-120 h | | | | | |
| Percent of Patients | 80.1 | 90.4 | 91.2 | 90.4 | 88.8 |
| Difference from Palo alone (%) | | 10.2 | 11.1 | 10.2 | 8.7 |
| p-value (*) | | 0.018 | 0.010 | 0.018 | 0.043 |

(*) p-value from logistic regression analysis, aprepitant p-value from post-hoc logistic regression analysis.

Table 6 summarizes results for main secondary endpoints. In the overall phase, 76.5% of patients in the palonosetron-alone group did not experience emesis, while 87.4%, 87.6, and 91.1% of patients did not experience emesis in the netupitant 100 mg., 200 mg. and 300 mg. combination groups, respectively (p<0.05 for all doses).

TABLE 6

SUMMARY OF SECONDARY EFFICACY
RESULTS: PERCENT OF PATIENTS, MFAS POPULATION

| Efficacy endpoint | Palo alone (n = 136) | Palo + Netu 100 mg (n = 135) | Palo + Netu 200 mg (n = 137) | Palo + Netu 300 mg (n = 135) | Aprepitant Regimen (N = 134) | Palo + Aprep 285 mg (N = 41)** |
|---|---|---|---|---|---|---|
| No Emesis | | | | | | |
| Overall | 76.5 | 87.4* | 87.6* | 91.1* | 87.3* | |
| Acute | 89.7 | 93.3 | 92.7 | 98.5* | 94.8 | |
| Delayed | 80.1 | 90.4* | 91.2* | 91.9* | 89.6* | |
| No Rescue | | | | | | |
| Overall | 95.6 | 97.8 | 100 | 98.5 | 97.8 | |
| Acute | 97.8 | 99.3 | 100 | 100 | 100 | |
| Delayed | 97.1 | 97.8 | 100 | 98.5 | 97.8 | |
| No Nausea | | | | | | |
| Overall | 50.7 | 54.8 | 62.0 | 61.5 | 58.2 | 32 |
| Acute | 75.0 | 72.6 | 77.4 | 80.0 | 77.6 | 59 |
| Delayed | 53.7 | 59.3 | 65.0 | 68.1* | 60.4 | 41 |
| No Significant Nausea | | | | | | |
| Overall | 79.4 | 80.0 | 86.1 | 89.6* | 85.8 | 56 |
| Acute | 93.4 | 94.1 | 94.2 | 98.5* | 94.0 | 79 |
| Delayed | 80.9 | 81.5 | 89.8* | 90.4* | 88.1 | 59 |
| Total Control | | | | | | |
| Overall | 50.0 | 54.8 | 61.3 | 59.3 | 56.0 | |
| Acute | 71.3 | 71.9 | 76.6 | 80.0 | 74.6 | |
| Delayed | 52.2 | 59.3 | 65.0* | 65.9* | 58.2 | |
| Complete Protection | | | | | | |
| Overall | 69.9 | 76.3 | 80.3* | 83.0* | 78.4 | 51 |
| Acute | 87.5 | 89.6 | 88.3 | 97.0* | 89.6 | 76 |
| Delayed | 73.5 | 80.0 | 87.6* | 84.4* | 82.1 | 66 |

*p-value < 0.05 compared with palonosetron-alone; aprepitant comparisons p-values calculated by post-hoc analysis
**As reported by Grunberg et al., Support Cancer Care (2009) 17: 589-594

Example 7

Comparative Results of Aprepitant Dosing Regimen

The following Table 8 reports the results observed for an aprepitant dosing regimen, as described in the FDA approved prescribing information for aprepitant, which demonstrates, among other things, that aprepitant has no meaningful effect on nausea. Table 7 reports the dosing regimen:

TABLE 7

| Treatment Regimen | Day 1 | Days 2 to 4 |
|---|---|---|
| Aprepitant | Aprepitant 125 mg PO | Aprepitant 80 mg PO Daily (Days 2 and 3 only) |
| | Dexamethasone 12 mg PO | |
| | Ondansetron 32 mg I.V. | |
| | | Dexamethasone 8 mg PO Daily (morning) |

TABLE 8

Percent of Patients Receiving Highly Emetogenic Chemotherapy
Responding by Treatment Group and Phase for Study 1 - Cycle 1

| ENDPOINTS | Aprepitant Regimen (N = 260)[†] % | Standard Therapy (N = 261)[†] % | p-Value |
|---|---|---|---|
| PRIMARY ENDPOINT | | | |
| Complete Response | | | |
| Overall[‡] | 73 | 52 | <0.001 |
| OTHER PRESPECIFIED ENDPOINTS | | | |
| Complete Response | | | |
| Acute phase[§] | 89 | 76 | <0.001 |
| Delayed phase[‖] | 75 | 56 | <0.001 |
| Complete Protection | | | |
| Overall | 63 | 49 | 0.001 |
| Acute phase | 85 | 75 | NS* |
| Delayed phase | 66 | 52 | <0.001 |

TABLE 8-continued

Percent of Patients Receiving Highly Emetogenic Chemotherapy Responding by Treatment Group and Phase for Study 1 - Cycle 1

| ENDPOINTS | Aprepitant Regimen (N = 260)† % | Standard Therapy (N = 261)† % | p-Value |
|---|---|---|---|
| No Emesia | | | |
| Overall | 78 | 55 | <0.001 |
| Acute phase | 90 | 79 | 0.001 |
| Delayed phase | 81 | 59 | <0.001 |
| No Nausea | | | |
| Overall | 48 | 44 | NS** |
| Delayed phase | 51 | 48 | NS** |
| No Significant Nausea | | | |
| Overall | 73 | 66 | NS** |
| Delayed phase | 75 | 69 | NS** |

†N: Number of patients (older than 18 years of age) who received cisplatin, study drug, and had at least one post-treatment efficacy evaluation.
‡Overall: 0 to 120 hours post-cisplatin treatment.
§Acute phase: 0 to 24 hours post-cisplatin treatment.
‖Delayed phase: 25 to 120 hours post-cisplatin treatment.
*Not statistically significant when adjusted for multiple comparisons.

Throughout this application, various publications are referenced. The disclosures of these publications in their entireties are hereby incorporated by reference into this application in order to more fully describe the state of the art to which this invention pertains. It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

The invention claimed is:

1. A method of treating both nausea and vomiting for five consecutive days in a patient in need thereof, comprising:
   a) administering to said patient on day one netupitant or a pharmaceutically acceptable salt thereof, in a therapeutically effective amount which enters the systemic circulation, crosses the blood brain barrier and occupies at least 70% of neurokinin-1 ($NK_1$) receptors in the striatum seventy-two hours after said administration;
   b) administering to said patient on day one a therapeutically effective amount of palonosetron or a pharmaceutically acceptable salt thereof; and
   c) administering to said patient on day one a first dose of dexamethasone which is ineffective against chemotherapy induced nausea and vomiting (CINV) when administered alone, but effective against CINV when administered in combination with said netupitant,
   wherein said first dose of dexamethasone comprises from 50 to 70% of a minimum effective dose when administered alone against CINV;
   steps a b and (c) are effective to treat both nausea and vomiting during the period defined by days one through five; and
   steps (a), (b) and (c) are effective to treat both nausea and vomiting to a greater extent during the period defined by days one through five than steps (b) and (c) alone.

2. The method of claim 1, further comprising: d) administering to said patient, on days two, three and four, a second dose of dexamethasone which is ineffective against vomiting when administered alone against vomiting, but effective against vomiting when administered in combination with steps (a) and (b), wherein said second dose comprises from 40 to 60% of a minimum effective dose when administered alone against vomiting.

3. The method of claim 1 or 2, wherein said netupitant occupies at least 80% of $NK_1$ receptors in the striatum seventy-two hours after said administration.

4. The method of claim 1, wherein only one dose of netupitant or a pharmaceutically acceptable salt thereof is administered during said five days.

5. The method of claim 1, wherein only one dose of netupitant or a pharmaceutically acceptable salt thereof is administered during said five days, and said one dose is administered orally.

6. The method of claim 1, wherein said therapeutically effective amount of netupitant comprises from about 200 to about 400 mg of netupitant or a pharmaceutically acceptable salt thereof.

7. The method of claim 1, wherein said therapeutically effective amount of netupitant comprises about 300 mg of netupitant as a free base.

8. The method of claim 1, wherein said therapeutically minimum effective dose of dexamethasone when administered alone comprises from about 16 mg to about 20 mg of dexamethasone.

9. The method of claim 1, wherein only one dose of said palonosetron or a pharmaceutically acceptable salt thereof is administered during said five days.

10. The method of claim 1, wherein said therapeutically effective amount of palonosetron or pharmaceutically acceptable salt thereof is from about 0.25 to about 0.75 mg based on the weight of the free base.

11. The method of claim 1, wherein said palonosetron is administered as palonosetron hydrochloride, and said therapeutically effective amount of said palonosetron hydrochloride is about 0.56 mg of palonosetron hydrochloride, corresponding to about 0.5 mg of palonosetron as a free base.

12. The method of claim 1, wherein said palonosetron is administered orally.

13. The method of claim 1, comprising orally administering:
   a) about 300 mg of netupitant as a free base on day one;
   b) about 0.56 mg of palonosetron hydrochloride, corresponding to about 0.5 mg of palonosetron as a free base, on day one; and
   c) about 12 mg of dexamethasone on day one.

14. The method of claim 1, comprising orally administering:
   a) about 300 mg of netupitant as a free base on day one;
   b) about 0.56 mg of palonosetron hydrochloride (corresponding to about 0.5 mg of palonosetron as a free base) on day one;
   c) about 12 mg of dexamethasone on day one; and
   d) about 8 mg of dexamethasone on days two, three and four.

15. The method of claim 1, wherein said nausea and vomiting is chemotherapy induced nausea and vomiting ("CINV"), radiation therapy induced nausea and vomiting ("RINV"), or post-operative nausea and vomiting ("PONV").

16. The method of claim 1, wherein said nausea and vomiting is induced by moderately or highly emetogenic chemotherapy.

17. The method of claim 1, comprising administering moderately or highly emetogenic chemotherapy within from about one hour to about two hours of said administration of said netupitant or pharmaceutically acceptable salt thereof.

18. The method of claim 1, comprising treating nausea and vomiting in response to highly emetogenic chemotherapy during the acute phase, or in response to highly emetogenic chemotherapy during the delayed phase, or in response to moderately emetogenic chemotherapy during the acute phase, or in response to moderately emetogenic chemotherapy during the delayed phase.

19. A method of treating both nausea and vomiting in a human subject in need thereof during the acute or delayed phases of chemotherapy induced nausea and vomiting (CINV) in response to moderately or highly emetogenic chemotherapy, comprising administering to said subject before said chemotherapy a therapeutically effective amount of netupitant or a pharmaceutically acceptable salt thereof and a therapeutically effective amount of palonosetron or a pharmaceutically acceptable salt thereof.

20. The method of claim 19, comprising orally administering from about 200 to about 400 mg of netupitant or a pharmaceutically acceptable salt thereof, and from about 0.25 to about 0.75 mg of palonosetron or a pharmaceutically acceptable salt thereof.

21. The method of claim 19, comprising orally administering about 300 mg of netupitant as the free base and about 0.56 mg of palonosetron hydrochloride.

22. The method of claim 19, further comprising, if said patient is undergoing highly emetogenic chemotherapy, administering a sub-therapeutic dose of dexamethasone on days one, two, three and four, wherein day one is the day on which netupitant and palonosetron, or pharmaceutically acceptable salts thereof, are administered.

23. The method of claim 19, further comprising, if said patient is undergoing highly emetogenic chemotherapy, orally administering 12 mg of dexamethasone on day one and 8 mg of dexamethasone on days two, three and four, wherein day one is the day on which netupitant and palonosetron, or pharmaceutically acceptable salts thereof, are administered.

24. The method of claim 1, wherein said netupitant or pharmaceutically acceptable salt thereof and said palonosetron or pharmaceutically acceptable salt thereof are synergistically effective to antagonize NK1 activity.

25. The method of claim 19, wherein said netupitant or pharmaceutically acceptable salt thereof and said palonosetron or pharmaceutically acceptable salt thereof are synergistically effective to antagonize NK1 activity.

* * * * *

UNITED STATES PATENT AND TRADEMARK OFFICE
CERTIFICATE OF CORRECTION

PATENT NO. : 8,623,826 B2  
APPLICATION NO. : 13/077462  
DATED : January 7, 2014  
INVENTOR(S) : Fabio Trento et al.

Page 1 of 1

It is certified that error appears in the above-identified patent and that said Letters Patent is hereby corrected as shown below:

On the Title Page, Related U.S. Application Data (item (63)), after "Continuation of application No." delete "PCT/US2010/057192 filed on Nov. 19, 2010", and insert --PCT/IB10/03106 filed on Nov. 18, 2010--

Signed and Sealed this  
Nineteenth Day of August, 2014

Michelle K. Lee  
*Deputy Director of the United States Patent and Trademark Office*